(12) United States Patent
Chawla

(10) Patent No.: US 9,486,315 B2
(45) Date of Patent: Nov. 8, 2016

(54) VALVE REPAIR INSTRUMENT

(76) Inventor: Surendra K. Chawla, West Hartford, CT (US)

( * ) Notice: Subject to any disclaimer, the term of this patent is extended or adjusted under 35 U.S.C. 154(b) by 894 days.

(21) Appl. No.: 13/176,127

(22) Filed: Jul. 5, 2011

(65) Prior Publication Data

US 2013/0013056 A1    Jan. 10, 2013

(51) Int. Cl.
*A61F 2/24* (2006.01)

(52) U.S. Cl.
CPC ........... *A61F 2/2457* (2013.01); *A61F 2/2463* (2013.01); *A61F 2/2466* (2013.01)

(58) Field of Classification Search
CPC ... A61F 2/2457; A61F 2/2463; A61F 2/2466
USPC ...... 623/2.1, 2.11, 2.34, 2.37; 606/108, 213, 606/190
See application file for complete search history.

(56) References Cited

U.S. PATENT DOCUMENTS 5,910,144 A * 6/1999 Hayashi .................. 606/108
6,575,971 B2 * 6/2003 Hauck et al. .................. 606/52

* cited by examiner

*Primary Examiner* — Vy Bui
(74) *Attorney, Agent, or Firm* — Cantor Colburn LLP

(57) ABSTRACT

A valve repair instrument and method of repair for the mitral valve of the heart is disclosed. The valve repair instrument includes an elongated body having two ends. One of the ends being configured to maintain a muscle portion of a valve repair device in an expanded position for attachment to the papillary muscle, the other end being configured to maintain a leaflet portion of a valve repair device in an expanded position for attachment to a valve leaflet. The valve repair device is attached to the diseased valve by suturing the leaflet portion to the affected leaflet and suturing the muscle portion to the affected muscle.

11 Claims, 10 Drawing Sheets

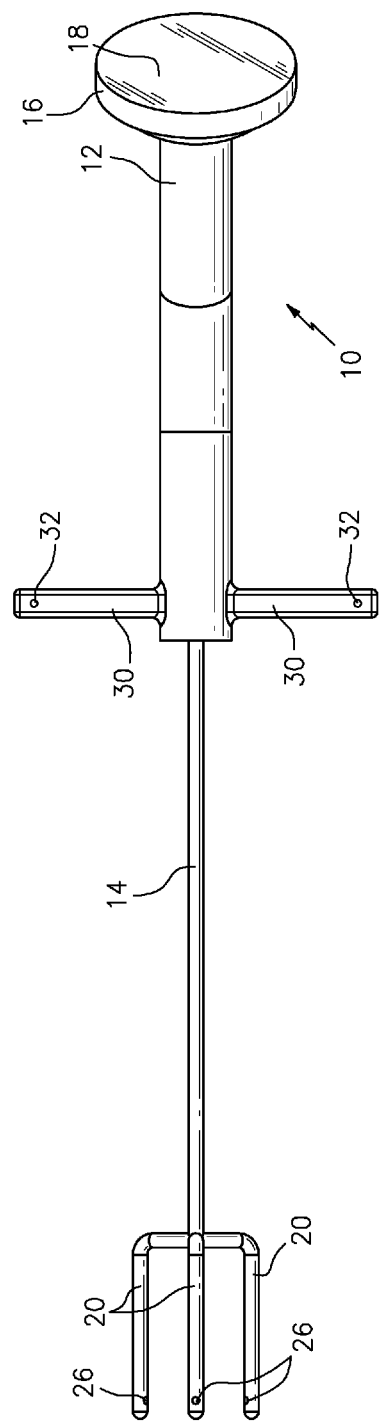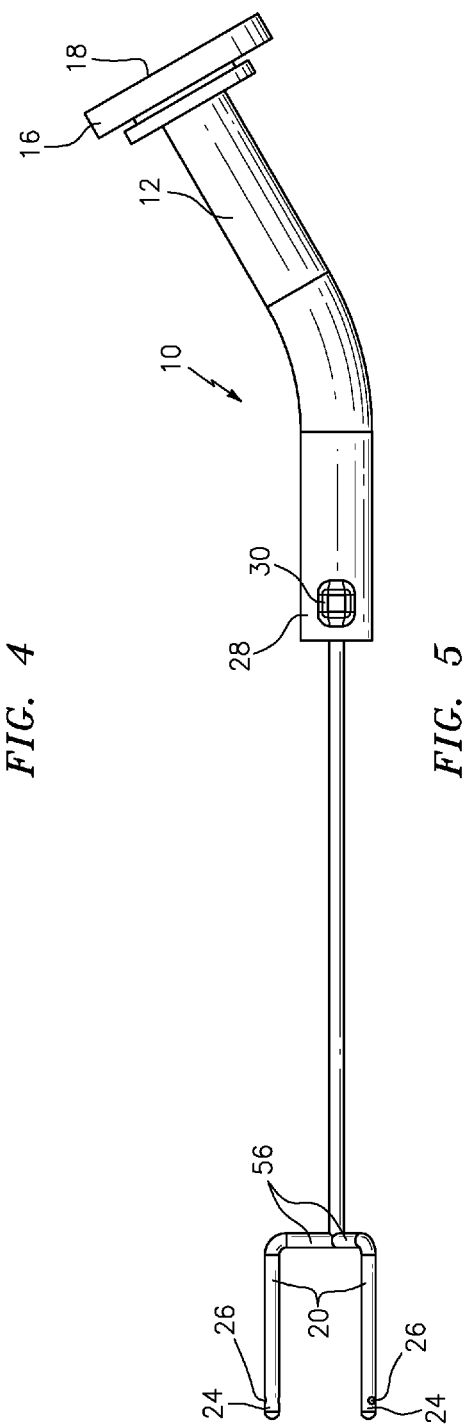

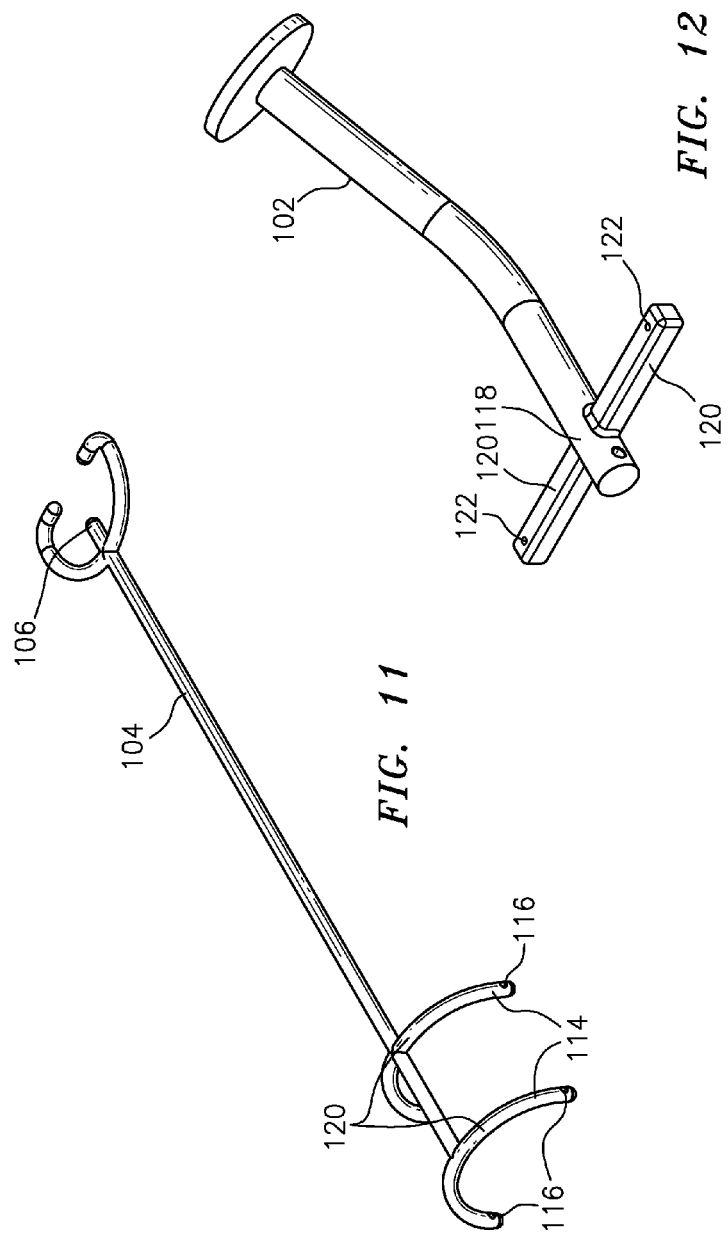

VALVE REPAIR INSTRUMENT

BACKGROUND OF THE INVENTION

The present disclosure relates to an instrument for the placement of a valve repair device and a method for repairing a heart valve. More particularly, this disclosure relates to an instrument useful in the repair of the mitral valve.

The human heart has four chambers and four one way valves. The right upper chamber, known as the right atrium, receives deoxygenated blood from the body and passes the blood to the right lower chamber, known as the right ventricle, through the tricuspid valve. The blood then passes through the pulmonary valve and is carried via the pulmonary arteries to the lungs for oxygenation. After the blood is oxygenated, it is received into the left side of the heart. The upper chamber, known as the left atrium, receives the blood from the lungs by four pulmonary veins, two from each lung. The blood is then passed to the left ventricle through the mitral valve. The main pumping chamber, the left ventricle, then pushes the blood to the body through the aortic valve.

The mitral valve is also known as a bicuspid valve, as it has two cusps or leaflets. The leaflets consist of the anterior leaflet, which is located adjacent to the aortic valve, and the posterior leaflet. The anterior leaflet is larger than the posterior leaflet. At the junction of the leaflets, each leaflet has a scalloped edge with three rounded portions, known as $A_1$, $A_2$, and $A_3$ for the anterior leaflet, and $P_1$, $P_2$ and $P_3$ for the posterior leaflet. The leaflets are attached to the papillary muscles by the chordae tendineae. The papillary muscles maintain the integrity of chordal leaflet alignment, preventing prolapse of the leaflets. The mitral valve allows blood to flow from the left atrium to the left ventricle but prevents blood from flowing back to the left atrium.

The tricuspid valve and the pulmonary valves are usually less affected by the disease process. Disease in the mitral valve and the aortic valve is more common in the affected adult population.

Mitral valve stenosis, for example, consists of an obstructive lesion to the leaflets of the valve. When the valves are narrow, also called "stenotic" valves, there is an obstruction to the flow of blood to the receiving chamber and an associated back up of blood. Dilatation of the left atrium develops and may be followed by right-sided heart failure and pulmonary edema, causing lung congestion and symptoms of shortness of breath. If the symptoms are severe, surgical intervention may be warranted.

Thickening and calcification is the commonest cause of narrowing of the mitral valve, secondary to the long-term effects of rheumatic disease. The incidence of mitral stenosis has decreased in the United States as the incidence of rheumatic fever has decreased as a result of the early institution of antibiotics. However, the leaking valve or the regurgitant valve incidence has increased in the last two decades. Mitral regurgitation is commonly due to degeneration or myxomatous disease leading to the lack of coaptation of the two mitral leaflets. The lack of coaptation in turn leads to the blood being regurgitated into the left upper chamber or the left atrium, causing pulmonary congestion and shortness of breath. Other causes include rupture of the chordae tendineae or the papillary muscles which are primarily needed to the support the two leaflets. Infection leading to the destruction of the valve leaflet or congenital clefts can also cause mitral regurgitation.

Treatments for these conditions have varied. Opening of the mitral valve was initiated in the 1950's in a closed method, known as a closed commisurotomy (separation of commissures by dialators). With the advent of heart-lung machine in 1955-56 by Dr. John H. Gibbons, Jr., open mitral commisurotomy was started with success.

Due to the high recurrence of stenosis, mitral valve replacement with prosthetic valves, typically constructed of a "ball and cage" (or ball valve), became the normal procedure in the 1960's, as proposed by Dr. Albert Starr. These valves were met with limited success as blood flow obstruction occurred with some frequency, leading to thromboembolism, causing strokes. Other attempts to replace the mitral valve were met with limited success. For example, Bjork Shiley valves were introduced as tilting disc valves to decrease the blood flow obstruction, but a flaw in the design led to strut fracture and their discontinuation. St. Jude valves, with a double tilting disc design, were introduced in the late 1970's. These valves have stood the test of durability and acceptable thromboembolism and are the preferred prosthetic valve replacement in the younger population.

Bioprosthesis valves, harvested from heterologous mammals, such as swine and bovine, have also been successfully employed, however, such valves frequently wear out due to degeneration and calcification. Moreover, the current designs for the mitral valve are somewhat limited due to the specific VORTEX flow of the left ventricle. U.S. Pat. No. 6,074,417 illustrates a total bioprosthesis mitral valve.

When possible, surgical repair of the defective valve is preferable over the prosthetic replacement. The thrust of surgical repair has been to preserve the integrity of the papillary muscle, the chordae tendineae and the leaflets. Numerous studies have proved this hypothesis in terms of long-term results and the avoidance of anticoagulation, which can cause life-threatening bleeding complications. In the 1980's, Dr. A F Carpentier of France, pioneered several methods to repair the mitral valve. Rupture of the chordae or the prolapse of the middle scallop of the posterior leaflet was easily repaired by excising the diseased piece, repairing the annulas, and suturing the two leaflets. This procedure has become a preferred method and has produced consistent results. These repairs are supported by the placement of a cloth-covered metallic ring to bring the annulus to the near normal level.

Despite the advancement in the surgical management of the posterior leaflet, the repair of the anterior mitral leaflet has proven more difficult. Various surgical techniques have been devised, but without consistent results. Chordal shortening, chordal transfer, triangular resection of the leaflet or transposing part of the posterior leaflet to the anterior leaflet, have been proposed. Recently the use of the prosthetic material "goretex" sutures have been used as artificial chordae, with some early success. *Long Term Results of Mitral Valve Repair for Myxomatous Disease with and without Chordal Replacement with Expanded Polytetrafluoroethylee*, The Journal of Thoracic and Cardiovascular Surgery, Jun. 1998, 1279-1286.

The use of prosthetic sutures for the anterior or posterior leaflet requires a great deal of skill on the part of the surgeon to make sure the sutures, duplicating the chords, are of the appropriate length. Moreover, attachment of the sutures to the leaflets and papillary muscles is delicate and cumbersome.

In U.S. Pat. No. 6,997,950, a valve repair device is disclosed that includes a leaflet portion, a muscle portion, and a plurality of chords connecting the leaflet portion to the muscle portion that can be sutured in place to effectuate a repair of the mitral valve.

BRIEF SUMMARY OF THE INVENTION

The above discussed and other drawbacks and deficiencies are overcome or alleviated by an instrument for the placement of a valve repair device and a method for repairing a heart valve.

The instrument supports a valve repair device in a configuration for attachment to the diseased valve by holding the leaflet portion and muscle portion in an expanded position so that it may be sutured in place.

As an additional feature, the instrument includes a shaft mounted within a hollow tube. The shaft includes a plurality of extension members at one end that hold the muscle portion in position for attachment to the papillary muscle. Upon separation of the muscle portion from the instrument, the shaft is retracted and the extension members are drawn into the tube. The leaflet portion is sutured and separated from the instrument. The instrument is then withdrawn.

As an additional feature, the extension members are configured to maintain the muscle portion in a semi-cylindrical shape for attachment to the papillary muscle.

As an additional feature, the instrument includes semicircular extension members configured to maintain the muscle portion in a semi-cylindrical shape for attachment to the papillary muscle.

As an additional feature, the extension members include an eyelet to retain a chord that secures the muscle portion to the instrument. The chord is severed to separate the muscle portion from the instrument and drawn into the tube when the shaft is retracted.

As an additional feature, the instrument includes a handle having opposed arms. The arms are configured to hold the leaflet portion in an extended position. The leaflet portion is attached to the arms by chords which are severed after the leaflet portion is sutured into place.

As an additional feature, the instrument is constructed of a distal portion and a proximal portion which are detachable.

BRIEF DESCRIPTION OF THE DRAWINGS

Referring to the FIGURES wherein the like elements are numbered alike in the several FIGURES

FIG. 4 shows a top view of the valve repair instrument;

FIG. 5 shows a side view of the valve repair instrument;

FIG. 11 illustrates the distal portion of the valve repair instrument shown in FIG. 10; and FIG. 12 illustrates the handle portion of the valve repair instrument shown in FIG. 10.

DETAILED DESCRIPTION OF THE DRAWINGS

Figure 1:
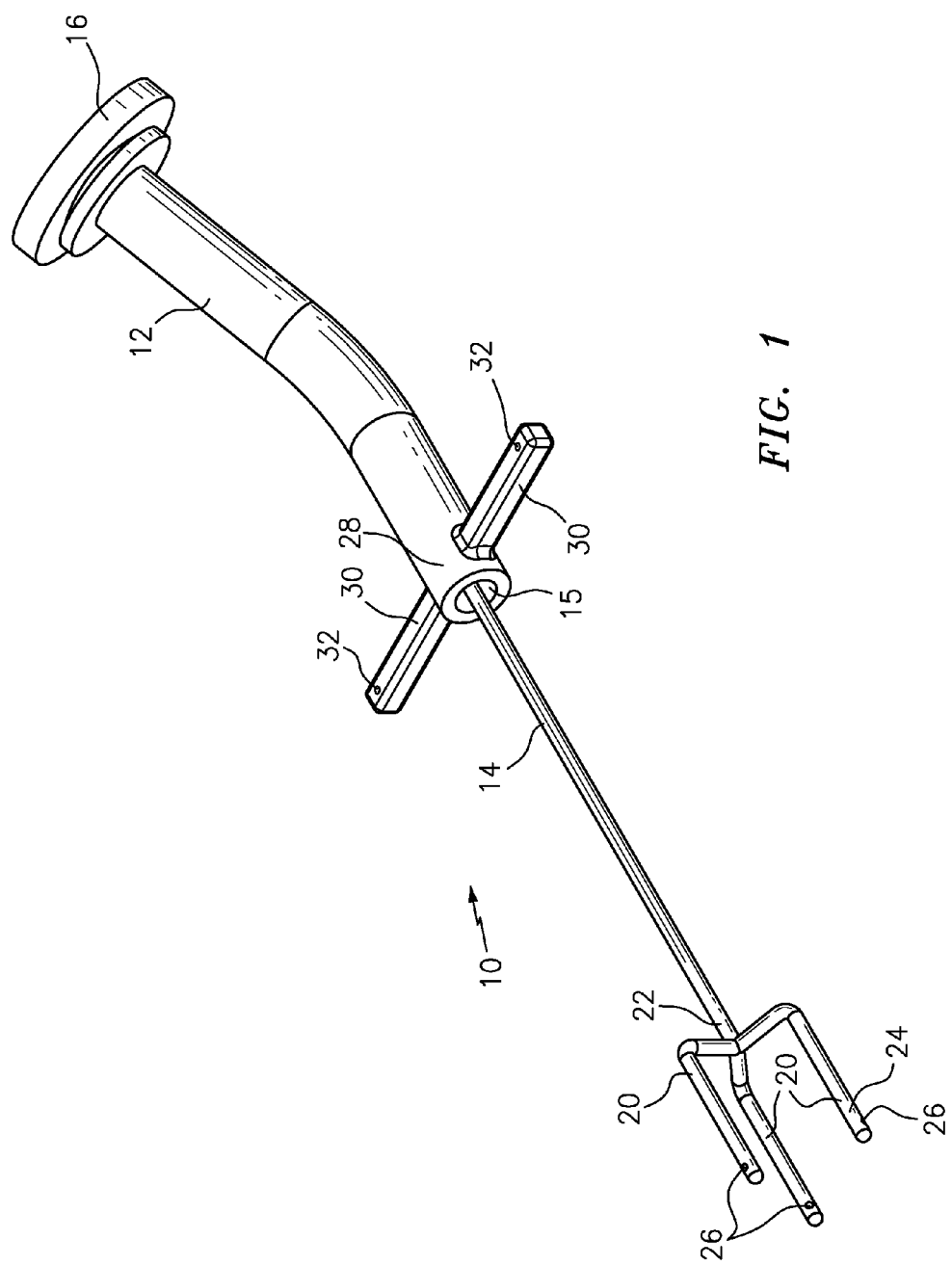
FIG. 1 shows a prospective view of the valve repair instrument.

Referring to FIG. 1, a valve repair instrument 10 in accordance with the present invention is illustrated. Valve repair instrument 10 includes a handle portion 12 and a shaft 14 slideably engaged within the handle portion 12. A knob 16 is disposed at the proximal end 18 of the shaft 14. A plurality of extension members 20 are disposed at the distal end 22 of the shaft 14. Extension members 20 are constructed of a flexible material, such as plastic, so that they are withdrawn into handle portion 12 when shaft 14 is removed. Extension members include a retaining portion 24 having a plurality of eyelets 26. Handle 12 includes a base 28 having opposed arms 30. Each arm includes an eyelet 32.

Figure 2:
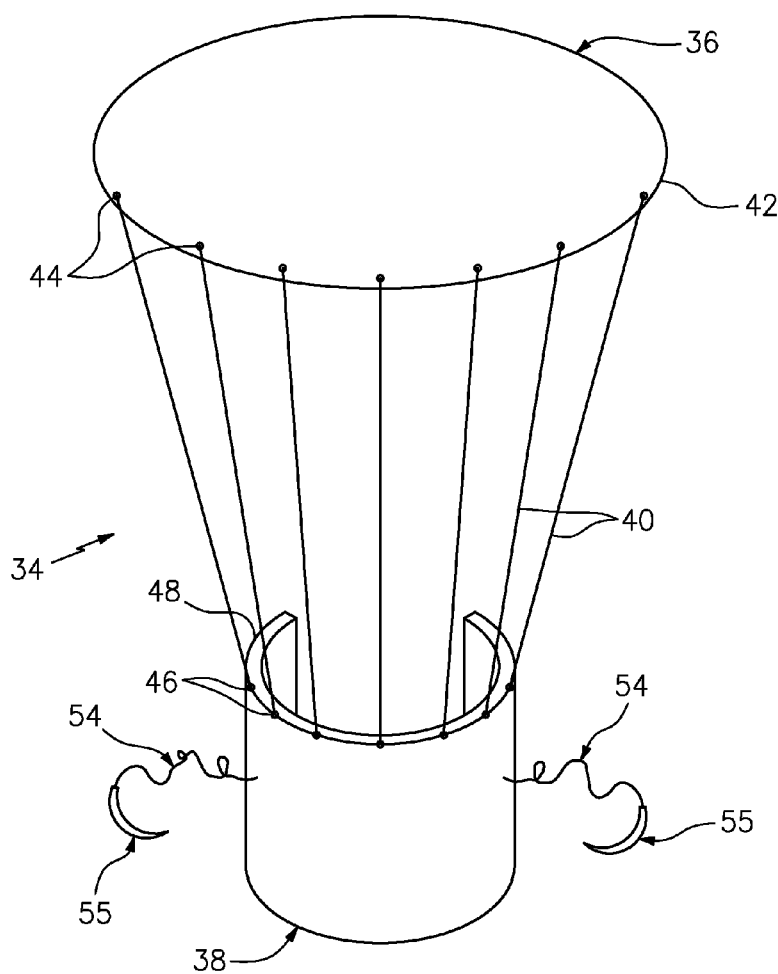
FIG. 2 shows a prospective view of the valve repair device in accordance with the prior art.

Referring to FIG. 2, a valve repair device 34 having a leaflet portion 36 and a muscle portion 38 is attached to the valve repair instrument 10. Valve repair device includes a plurality of chords 40. Chords 40 extend from the leaflet portion 36 and are attached to the leaflet portion 36 adjacent end 42 at a plurality of attachment locations 44. Chords 40 connect leaflet portion 36 to a muscle portion 38 at a plurality of respective attachment locations 46 adjacent end 48 of muscle portion 38. An example of such a valve repair device is shown in U.S. Pat. No. 6,997,950 which is incorporated herein by reference.

Figure 3:
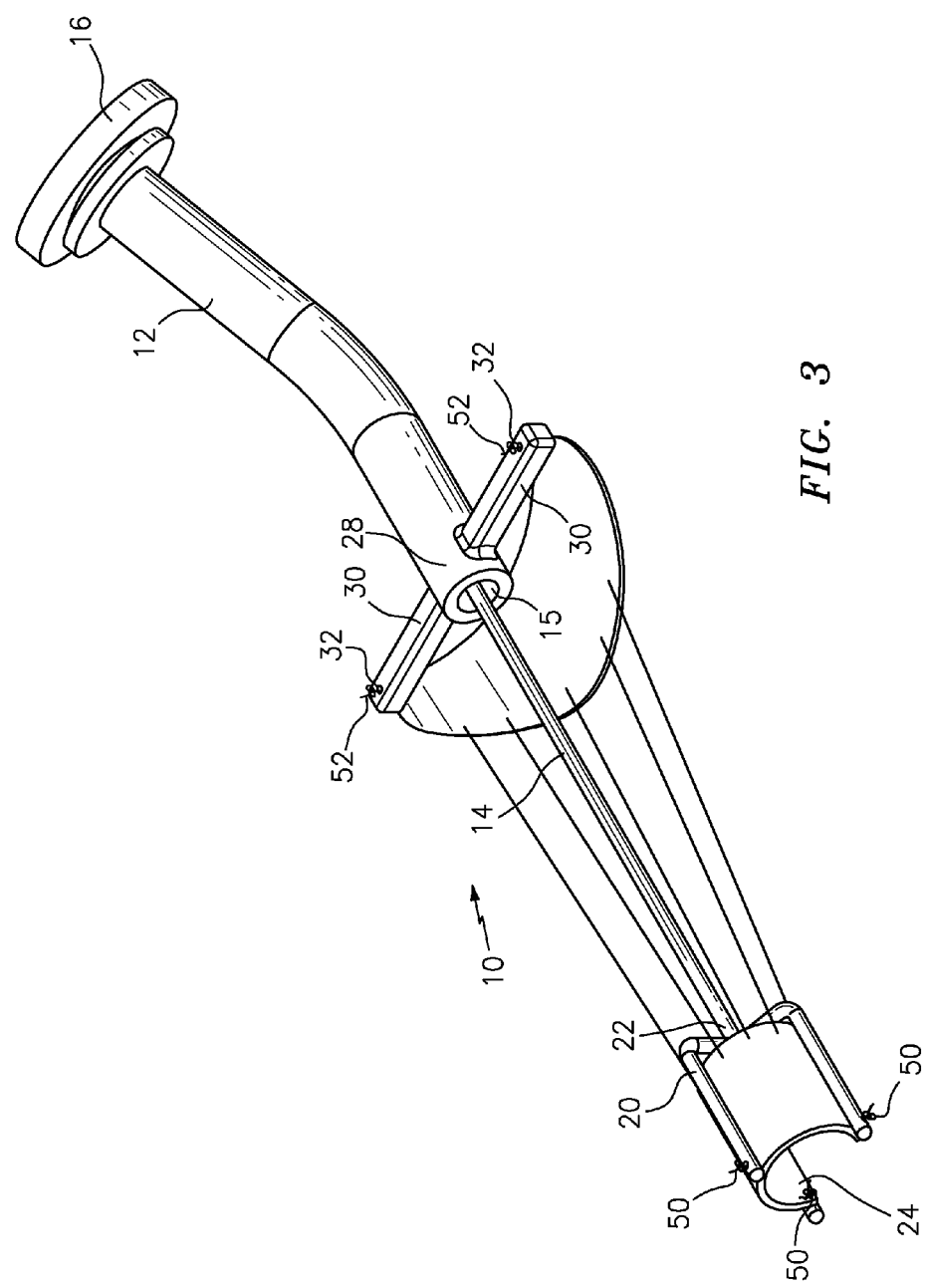
FIG. 3 shows a prospective view of the valve repair instrument with the valve repair device attached.

Turning now to FIG. 3, with reference to FIG. 2, a prospective view of the valve repair instrument 10 with the valve repair device 34 attached thereto is illustrated. As explained in greater detail below, valve repair instrument 10 maintains the valve repair device 34 in an expanded position for attachment to the papillary muscle and affected leaflet of the human heart. The muscle portion 38 is attached to the retaining portions 24 by chords 50 which are secured to the respective eyelets 26. Leaflet portion 36 is attached to the handle 12 by chords 52 at the respective eyelets 32. In use, the distal end 22 of the valve repair instrument 10 is placed such that the muscle portion 38 is positioned against the papillary muscle. Muscle portion 38 is then sutured to the papillary muscle with sutures 54. Needles 55 are pre-attached to sutures 54. Alternatively, separate needles may be used to attach the sutures 54 to the papillary muscle. Chords 50 are then severed allowing extension members 20 to be separated from the valve repair device 34. Knob 16 is then pulled, causing shaft 14 to retract into handle 12. Extension members 20 compress and retract into handle 12. The leaflet portion 36 of the valve repair device 34 is then sutured to the affected leaflet. Chords 52 are then severed allowing leaflet portion 36 to be separated from the valve repair instrument 10.

Turning now to FIG. 4, a top view of valve repair instrument 10 is shown. The extension members 20 may be placed such that the muscle portion 38 is held in a semi-cylindrical shape. In this manner the muscle portion 38 may be slide over the papillary muscle as the valve repair device is positioned for operation. Preferably the opposing extension members 20 are spaced slightly less than 180 degrees so that muscle portion 38 is not attached to the extension members at its outer periphery, allowing sutures 54, which attach the muscle portion 38 to the papillary muscle, to be more easily accessed during operation. Handle portion 12 includes a pair of opposed arms 30 to maintaining the leaflet portion 36 in place via chords 52. Handle portion 12 may optionally be constructed with a syringe shaped body, having a center bore 15 there through. Shaft 14 includes a knob 16 at the proximal end 18. Knob 16 is configured to that it may be grasped to pull the shaft 14 away from the handle 12 to remove the shaft 14 from the instrument 10.

Referring now to FIG. 5, a side view of the valve repair instrument 10 is shown. Extension members 20 include retention portion 24. Preferably, retaining portions 24 are generally parallel to shaft 14 to assist in maintaining the muscle portion 38 in a semi-cylindrical shape prior to use. Retaining portions 24 are constructed to deflect into handle 12 as the shaft 14 is retracted and may include a hinge or recess 56. Extension members 20 may include an internal passage for the placement of chords 50 to attach muscle portion 38 to retaining portions 24 at the respective eyelets 26. In use, after the muscle portion 38 is placed over the papillary muscle at the desired location and sutured in place, chords 54 are severed to separate the muscle portion 38 from the instrument 10. The user then pulls the knob 16 away from the handle 12, the retention portions 24 and respective chords 50 are drawn into the handle 12. The shaft 14 is completely removed from instrument 10. The base 28 is positioned so that the arms 30 retaining the leaflet portion 36 is placed to effectuate the repair of the leaflet by attachment of the leaflet portion 36 via sutures. Chords 52 are then severed and instrument 10 is removed.

Figure 6:
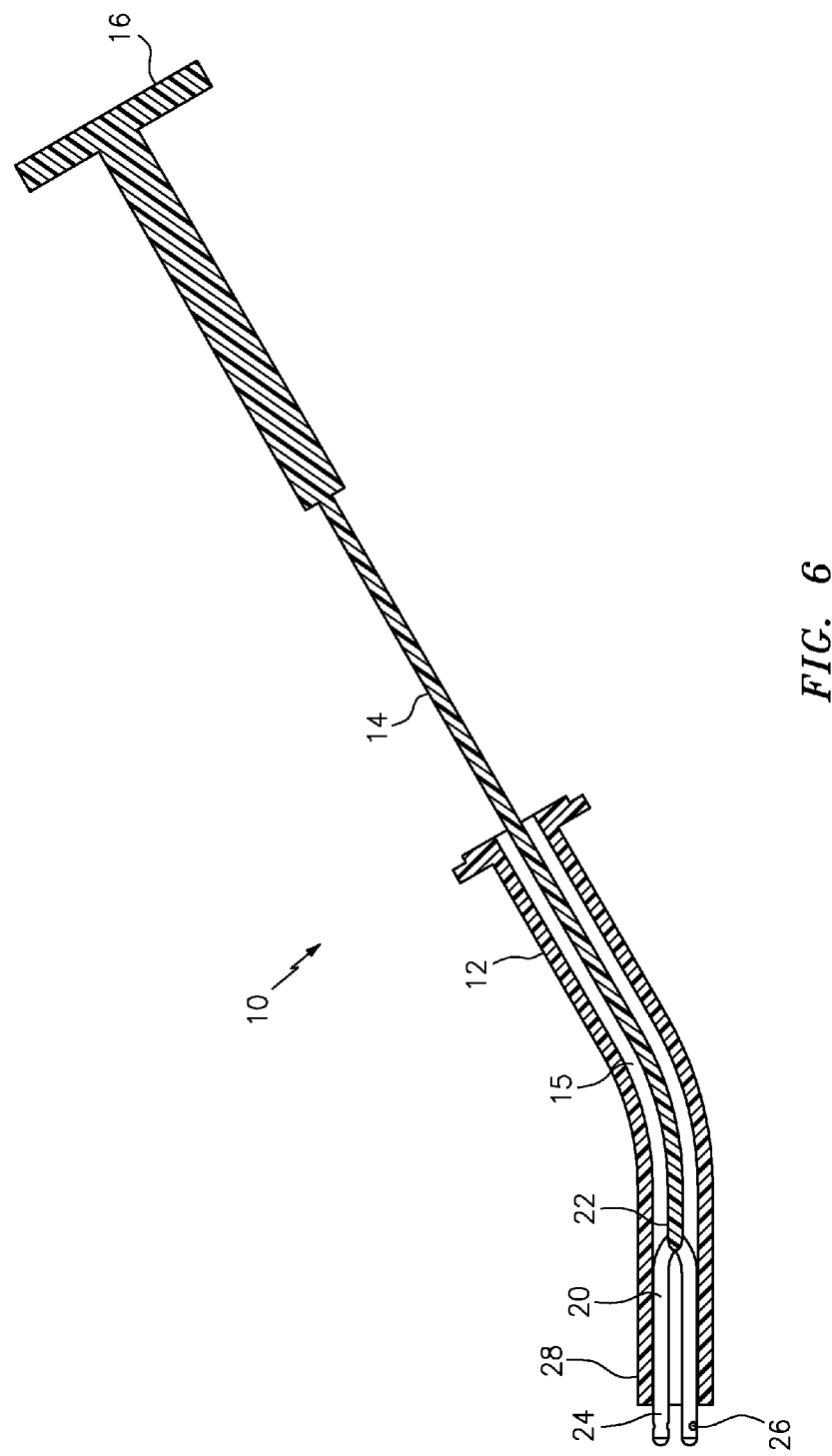
FIG. 6 shows a cross-sectional view of the valve repair instrument in a retracted position.

As shown in FIGS. 5 and 6, handle portion 12 includes a center bore 15 which is sized to receive the shaft 14 and the extension members 20 in a folded or compressed position. Preferably, handle 12 is slightly curved to assist in the entry into the heart through the left atrium. In use, after muscle portion 38 of the valve repair device 34 is sutured to the papillary muscle, and chords 50 are severed to separate the muscle portion 38 from the instrument 10, shaft 14 is withdrawn into handle 12. As shaft 14 is withdrawn into handle 12, extension members 20 are compress together and drawn into the shaft 14 via bore 15. Shaft 14 includes a knob 16 at the distal end 22 to assist the user in pulling shaft 14 into handle 12. Extension members 20 are withdrawn into the shaft 14. The shaft 14 is removed from the instrument 10. The chords 50 are drawn into the handle 12 with the extension members 20 and shaft 14.

Figure 7:
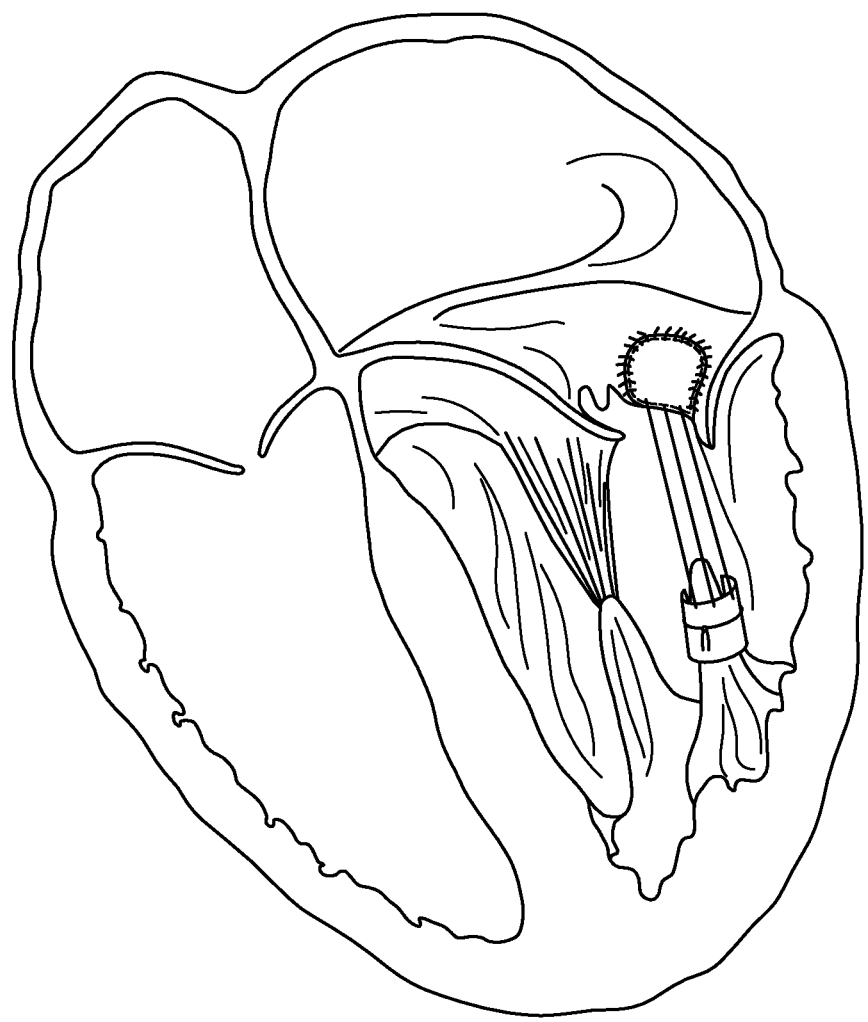
FIG. 7 illustrates a prior art cross sectional view of the heart, illustrating the mitral valve of the heart, illustrating a prior art valve repair device sutured in the mitral valve.
Figure 8:
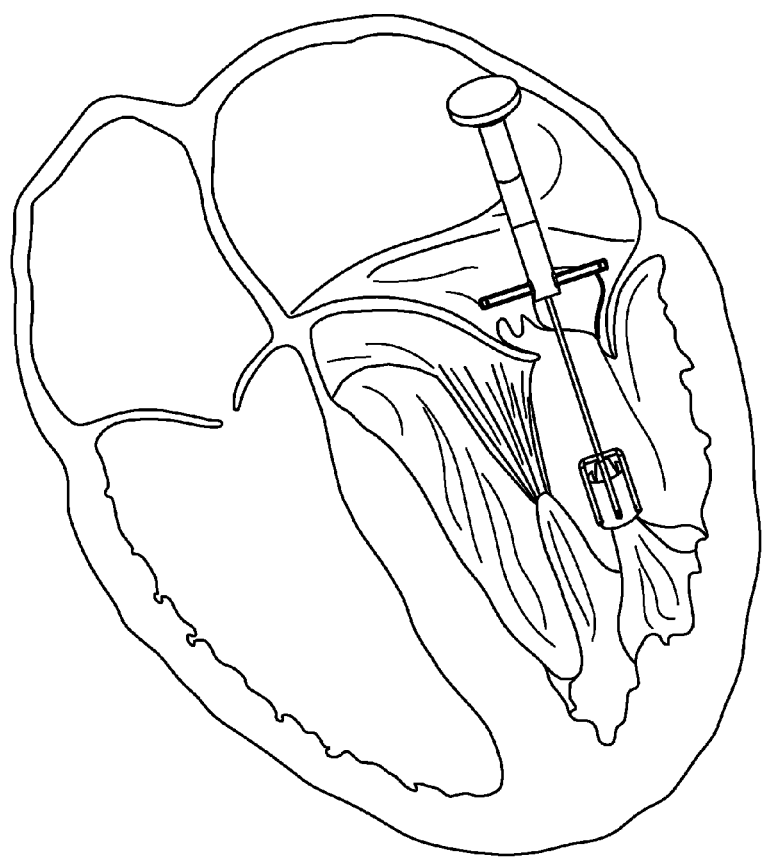
FIG. 8 shows a prospective view of the valve repair instrument placed in the heart with valve repair device.

Referring to FIGS. 1 though 8, the repair of the anterior leaflet of the mitral valve of the heart with valve repair instrument 10 is illustrated. As shown in prior art FIG. 7, the chordae tendineae are attached to the respective posterior leaflet or anterior leaflet and connect the leaflet to the papillary muscle. During a typical repair of the mitral valve, the diseased portion of the valve is excised, such as the elongated portion of a chordae or a ruptured chordae, and the remaining leaflet material is then sutured together. If the chordae tendineae is diseased, it may also be excised, with sutures connecting the leaflet to the papillary muscle. During open-heart surgery, the physician will assess the degree of disease, and determine the extent of the repair to the mitral valve needed. The surgeon will first excise the diseased material, such as the elongated scallop portion of a leaflet, the perforated portion of the leaflet, the affected chordae tendineae, etc. An annular ring may be used to reinforce the mitral valve. Next, the surgeon will determine the size of the valve repair device 34 needed to effectuate the repair and may reduce the leaflet by cutting. The physician also cuts unneeded chords 40.

In order to accurately determine the location, the surgeon may estimate the needed chord length by comparing the relative length of the adjoining chords. The chordae tendineae comprise the marginal chord, the secondary chord and the basilar chord. The marginal chord is located adjacent the margin or edge of the respective anterior or posterior leaflet. The basilar chord is located adjacent to the area adjoining the annulus of the mitral valve and the secondary chord is positioned between the marginal chord and the basilar chord. Disease in the mitral valve is typically associated with the marginal chord. Subsequent to its removal, the surgeon may approximate the needed chord length, by positioning the valve repair instrument 10 with the valve repair device 34 adjacent to a normal marginal chord. The surgeon may also reference the chord length of the opposing anterior or posterior leaflet chordae tendineae. Preferably, the surgeon will suture a holding stitch or a stay suture between the anterior and posterior leaflets at the level of adjoining normal chordae to obtain accurate approximation of the desired chord length.

Valve repair device 10 maintains the valve repair device 34 is an expanded position (FIG. 3). The distal end 22 of the instrument 10 is placed such that the muscle portion 38 is adjacent to the papillary muscle. Muscle portion 38 is maintained in a semi-cylindrical shape, allowing the surgeon to place the muscle portion 38 to partially surround the papillary muscle. In this manner, the instrument is positioned such that the muscle portion 38 is positioned for suturing to the papillary muscle via sutures 54. The chords 50 are then severed, separating the muscle portion 38 of the valve repair device 34 from the instrument 10. The extension members 20 and chords 50 may now be withdrawn from the instrument 10 prior to the attachment of the leaflet portion 36. The shaft 14 is grasped by the knob 16 and is withdrawn from the instrument 10 by pulling knob 16 and removing the shaft 14. The extension members 20 fold or compress into the handle 12 as the shaft 14 is withdrawn and then exit the handle 12 for removal from the instrument 10.

The handle portion 12 is then positioned such that the leaflet portion 36 is in place for repair of the affected leaflet. The leaflet portion 36 is attached to the arms 30 of the handle portion via chords 52. In this manner, the leaflet portion 36 is maintained in an expanded position. Once the leaflet portion is sutured in place, chords 52 are severed, and the leaflet portion 36 is separated from the instrument 10. Instrument 10 is then withdrawn.

The valve repair instrument 10 and valve repair device 34 may be used to repair the anterior leaflet or the posterior leaflet. Moreover, valve repair instrument 10 and valve repair device 34 may be offered in a variety of sizes and specifically in a kit form. Prior to undertaking the repair of the mitral valve, the surgeon will typically be acquainted with patient's specific physiology. During the open-heart operation, time is an important factor, and a surgeon may be confronted with an unknown defect in the valve. In use, valve repair instrument 10 and valve repair device 34 eliminates the bulky process of affixing sutures from the papillary muscle to the respective posterior or anterior leaflet.

Figure 9:
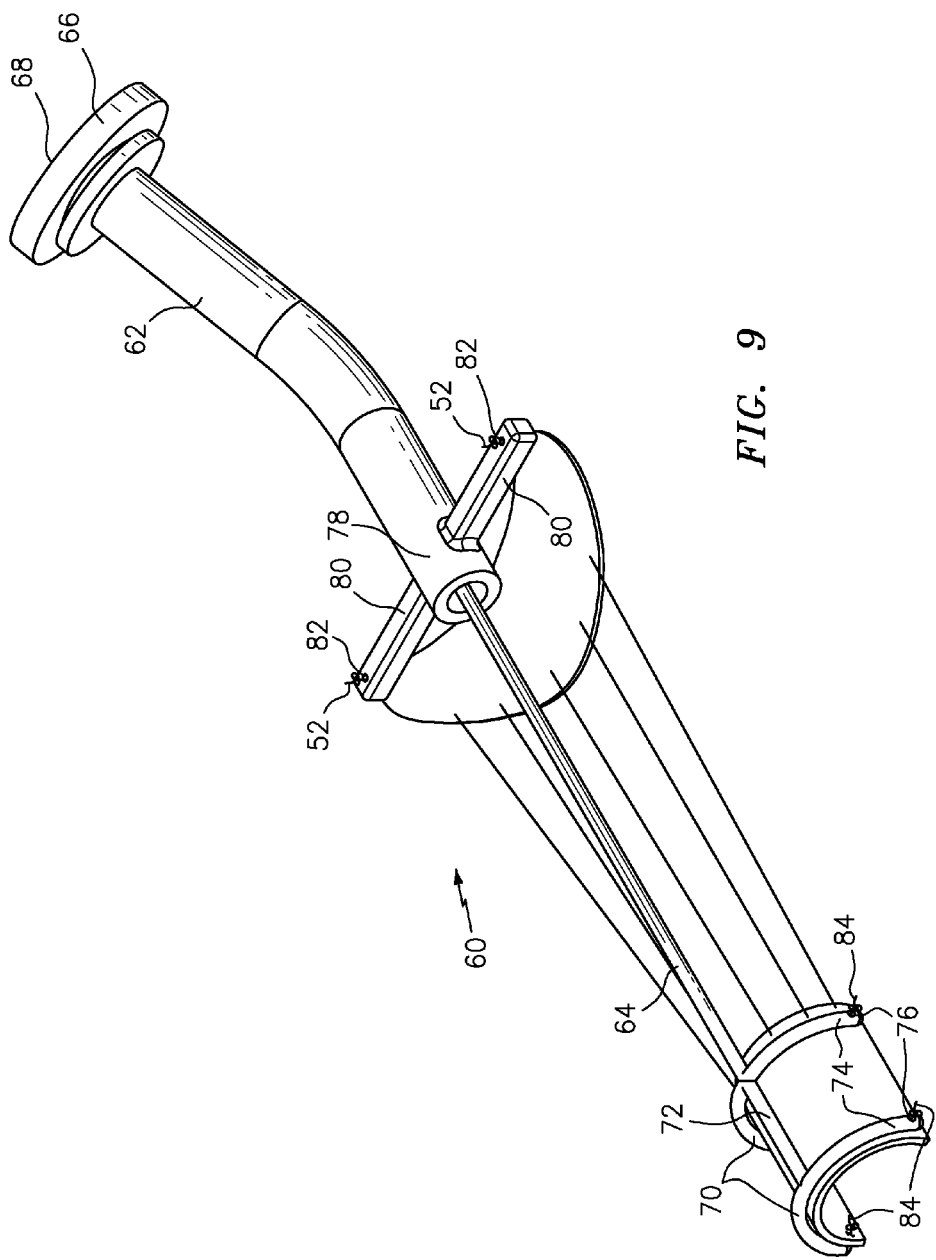
FIG. 9 illustrates a prospective view of another embodiment of the valve repair instrument with the valve repair device attached in accordance with the invention.

Referring to FIG. 9, another embodiment of the valve repair instrument 60 is shown. Valve repair instrument 60 includes a handle portion 62 and a shaft 64 slideably engaged within the handle portion 62. A knob 66 is disposed at the proximal end 68 of the shaft 64. A plurality of extension members 70 are disposed at the distal end 72 of the shaft 64. Extension members 70 are constructed of a flexible material, such as plastic, so that they are withdrawn into handle portion 62 when shaft 64 is removed. Extension members include a retaining portion 74 having a plurality of eyelets 76. Preferably, in this embodiment, extension members 70 are C-shaped. Handle 62 includes a base 78 having opposed arms 80. Each arm includes an eyelet 82. Extension members 70 may be hingedly connected to shaft 64 for compression into handle 62.

With reference to FIGS. 2 and 9, valve repair instrument 60 maintains the valve repair device 34 in an expanded position for attachment to the papillary muscle and affected leaflet of the human heart. The muscle portion 38 is attached to the retaining portions 74 by chords 84 which are secured to the respective eyelets 76. Leaflet portion 36 is attached to the handle 62 by chords 86 at the respective eyelets 82. In use, the distal end 72 of the valve repair instrument 60 is placed such that the muscle portion 38 is positioned against the papillary muscle. Muscle portion 38 is then sutured to the papillary muscle with sutures 54. Needles 55 are attached to sutures 54. Chords 84 are then severed allowing extension members 70 to be separated from the valve repair device 34. Knob 16 is then pulled, causing shaft 14 to retract into handle 12. Extension members 70 compress and retract into handle 62. The leaflet portion 36 of the valve repair device 34 is then sutured to the affected leaflet. Chords 86 are then severed allowing leaflet portion 36 to be separated from the valve repair instrument 60. Valve repair instrument 60 is then removed.

Figure 10:
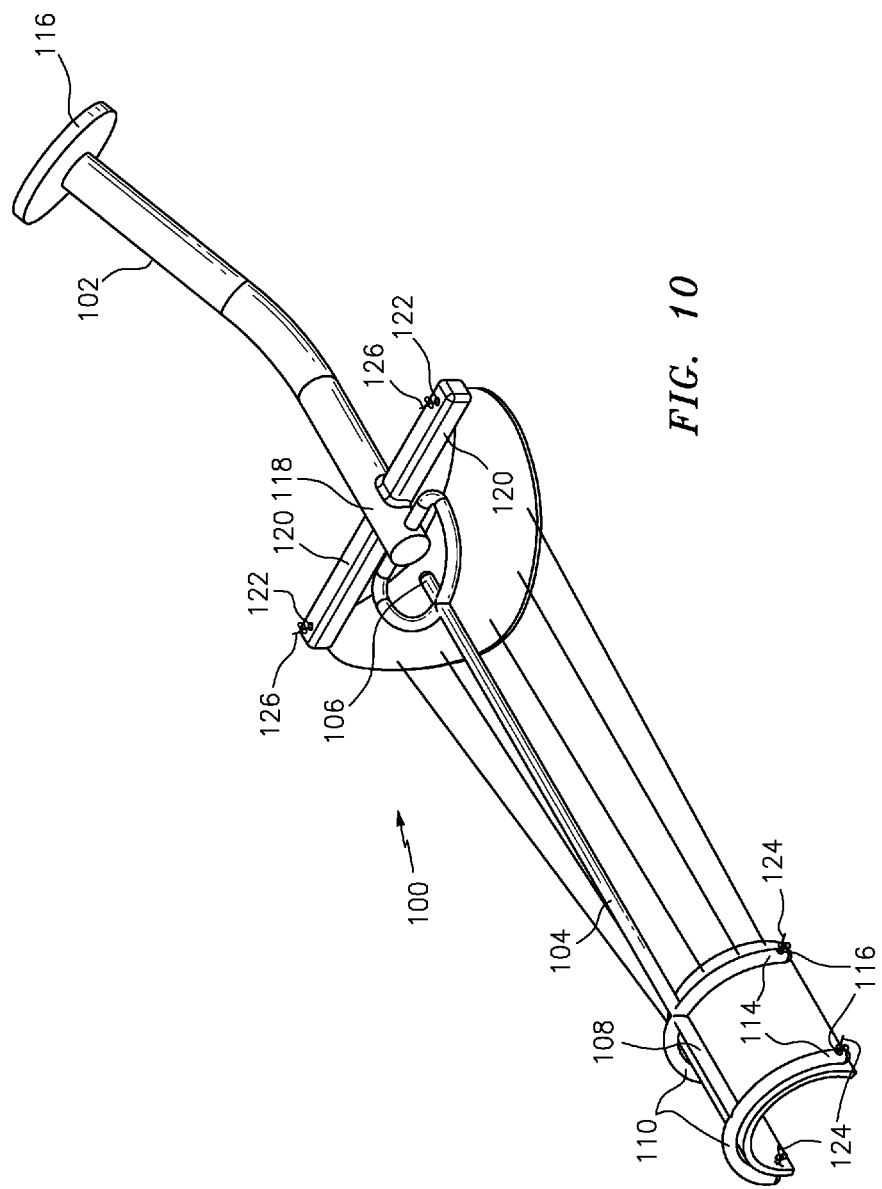
FIG. 10 illustrates a prospective view of another embodiment of the valve repair instrument with the valve repair device attached in accordance with the invention.

As shown in FIG. 10, and with reference to FIG. 2, another embodiment of the valve repair instrument 100 with a valve repair device 34 attached thereto is shown. Valve repair instrument maintains the valve repair device 34 in an expanded position and includes a handle portion 102 and a shaft 104. Handle portion 102 and a shaft 104 are detachable. A knob 106 is disposed at the proximal end 108 of the shaft 104. A plurality of extension members 110 are disposed at the distal end 112 of the shaft 104. Extension members 110 include a retaining portion 114 having a plurality of eyelets 116. Preferably, in this embodiment, extension members 110 are C-shaped. Handle 102 includes a base 118 having opposed arms 120. Each arm includes an eyelet 122.

With reference to FIGS. 2 and 10, valve repair instrument 100 maintains the valve repair device 34 in an expanded position for attachment to the papillary muscle and affected leaflet of the human heart. The muscle portion 38 is attached to the retaining portions 110 by chords 124 which are secured to the respective eyelets 116. Leaflet portion 36 is attached to the handle 102 by chords 126 at the respective eyelets 122. In use, the distal end 112 of the valve repair instrument 100 is placed such that the muscle portion 38 is positioned against the papillary muscle. Muscle portion 38 is then sutured to the papillary muscle with sutures 54. Needles 55 are attached to sutures 54. Chords 124 are then severed allowing extension members 110 to be separated from the valve repair device 34. The handle 102 and shaft 104 are then grasped such as with forceps, causing shaft 104 to separate from handle 102. Shaft 104 is then removed from the heart. The leaflet portion 36 of the valve repair device 34 is then sutured to the affected leaflet. Chords 126 are then severed allowing leaflet portion 36 to be separated from the valve repair instrument 100. Valve repair instrument 100 is then removed. As shown in FIGS. 11 and 12, shaft 104 includes a retaining portion 128 at its proximal end 130, having opposing fingers 132 to detachably connect shaft 104 to handle 102. Fingers 132 are received in openings 134 of handle 102. In this manner the shaft 104 and handle can be separated after the muscle portion 38 is separated from the extension members 110 during use.

The valve repair instrument 10 reduces the time necessary to place the valve repair device, such as valve repair device 34, by maintaining the valve repair device 34 in an expanded position for suturing. The valve repair instrument 10 also simplifies the mitral valve repair operation by allowing the surgeon to quickly place the instrument into position, thereby reducing the amount of time the patient is maintaining on the heart and lung machine.

While the invention has been described with reference to a preferred embodiment, it will be understood by those skilled in the art that various changes may be made and equivalents may be substituted for elements thereof without departing from the scope of the invention. In addition, many modifications may be made to adapt the invention to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A valve repair instrument, comprising:
   an elongated body, said elongated body having two ends;
   said first end having a plurality of extension members configured to maintain the muscle portion of a valve repair device in an expanded position for attachment to the papillary muscle, at least one of said extension members having an eyelet for receiving a retention chord for removably attaching the muscle portion to the first end;
   said second end being configured to maintain a leaflet portion of a valve repair device for attachment to a valve leaflet, at least one end of said second end having an eyelet for receiving a retention chord for removably attaching the leaflet portion of the second end.

2. A valve repair instrument according to claim 1, wherein said elongated body includes a handle and a shaft mounted for movement within said handle.

3. A valve repair instrument according to claim 2, wherein said distal end of said shaft includes a plurality of extension members that maintain said muscle portion in an expanded semi-circular position.

4. A valve repair instrument according to claim 3, wherein said handle includes a passage way and said extension members compress into said passage way.

5. A valve repair instrument according to claim 2, wherein said handle includes opposed arms, said leaflet portion being attached to said arms.

6. A valve repair instrument comprising:
   a tubular member; and
   a shaft mounted for movement within said tubular member, said shaft having a distal end, said distal end having at least one eyelet to maintain a muscle portion of a valve repair device in an expanded configuration for attachment to the papillary muscle, said distal end being retracted into said tubular member after attachment of said muscle portion;
   wherein at least one end of a proximal end portion of the valve repair instrument has an eyelet for receiving a retention chord for removably attaching a leaflet portion to the proximal end portion.

7. A valve repair instrument according to claim 6, wherein said distal end includes a plurality of extension members, said extension members being compressed into said tubular member after attachment of said muscle portion.

8. A valve repair instrument according to claim 7, wherein said extension members include retaining portions, each of said retaining portions having an eyelet for receiving a chord.

9. A valve repair instrument according to claim 8, wherein said retaining portions maintain said muscle portion in an expanded position to allow said muscle portion to at least partially surround the papillary muscle.

10. A valve repair instrument according to claim 6, wherein said tubular member Includes opposed arms, said arms being configured to maintain a leaflet portion of a valve repair device in an expanded position.

11. A valve repair instrument according to claim 10, wherein one of said arms includes an eyelet for receiving a retaining chord for removably attaching the leaflet portion.

* * * * *